United States Patent [19]

Harris et al.

[11] Patent Number: 4,683,430

[45] Date of Patent: Jul. 28, 1987

[54] EDDY CURRENT FLAW DETECTOR METHOD AND APPARATUS HAVING A ROTATABLE HIGH PERMEABILITY FLUX CONCENTRATOR ENCIRCLING A WORKPIECE

[75] Inventors: Richard M. Harris, North Royalton; Richard F. Abramczyk, Brunswick, both of Ohio

[73] Assignee: Republic Steel Corporation, Cleveland, Ohio

[21] Appl. No.: 625,033

[22] Filed: Jun. 27, 1984

[51] Int. Cl.⁴ .................... G01N 27/82; G01R 33/12
[52] U.S. Cl. ................................. 324/241; 324/240; 324/243
[58] Field of Search ............... 324/228, 236, 237, 238, 324/239, 240, 241, 242, 243

[56] References Cited

U.S. PATENT DOCUMENTS

| | | | |
|---|---|---|---|
| 2,104,646 | 1/1938 | Greenslade | 324/219 |
| 2,863,546 | 12/1950 | Josefowicz | 193/32 |
| 3,110,860 | 11/1963 | Allen | 324/226 |
| 3,152,302 | 10/1964 | Allen et al. | 324/226 |
| 3,916,301 | 10/1975 | Vild et al. | 324/233 |
| 4,002,967 | 1/1977 | Fennell et al. | 324/238 |
| 4,087,748 | 2/1978 | Pigeon et al. | 324/220 |
| 4,203,069 | 5/1980 | Davis | 324/220 |
| 4,355,281 | 10/1982 | Toth et al. | 324/232 |

FOREIGN PATENT DOCUMENTS 565248  8/1977  U.S.S.R. ................................ 324/240

Primary Examiner—Reinhard J. Eisenzopf
Assistant Examiner—Walter E. Snow
Attorney, Agent, or Firm—Watts, Hoffmann, Fisher & Heinke Co.

[57] ABSTRACT

Eddy current test apparatus of the type that generates eddy currents in an object and that senses flaws or defects by sensing changes in the induced eddy current. Two differential encircling coils surround a moving workpiece moving relative to said coils. One of the two test coils has an enclosed tubular pathway forming a loop adjacent to the coil. A steel ball is placed in the enclosed tubular pathway and is air driven through the pathway so that it continuously revolves in close proximity to the coil. The steel ball disrupts the magnetic field flux generated by the test coil in the workpiece. This disruption modifies the eddy current in the workpiece which in turn induces a well defined output signal in the test coil. In an alternate and preferred embodiment, two ferrite object are rotated near the two encircling coils to disrupt the eddy currents produced by both coils. The ferrite objects are radially offset so that they do not disrupt the magnetic field near a flaw at the same time.

5 Claims, 12 Drawing Figures

.010 SEAM 40KHZ

.020 SEAM 40KHZ

EDDY CURRENT FLAW DETECTOR METHOD AND APPARATUS HAVING A ROTATABLE HIGH PERMEABILITY FLUX CONCENTRATOR ENCIRCLING A WORKPIECE

DESCRIPTION

1. Technical Field

The present invention relates to an eddy current tester for detecting flaws along the surface of an elongated workpiece such as a steel bar or pipe.

2. Background Art

In the production of steel products it is desirable to detect manufacturing flaws as soon as possible so that remedial steps can be taken to eliminate the cause of those flaws, and to repair a flawed workpiece or steps in manufacturing steel are well documented and will not be described in detail. Briefly, molten iron is treated with oxygen and other agents are added in varying amounts to produce molten steel which is poured into molds to produce ingots or a continuous caster to produce slabs or billets. These billets are in turn heated and shaped into a bloom, a large block of steel anywhere from 10 to 16 inches in thickness and 20 to 30 feet in length. These blooms are stored and reheated when further shaping is desired. To make steel bars, the bloom is first formed into a billet which is a square typically 2 to 6 inches in cross-section and approximately 30 feet long.

The billet is heated to a temperature of approximately 2300°–2400° F. so that it becomes pliable enough to be rolled into a bar shape. The rolling process first produces an elliptical shaped bar which is gradually rounded as it passes through subsequent rolling stages. After the billet has been rolled, it is much longer and narrower. By way of example, a 5" cross-section billet can be rolled into a round steel bar approximately $\frac{5}{8}$" in diameter and hundreds of feet long. The steel bar is then cut into pieces of a desired length for shipment.

Various inspection steps are performed on the billet prior to rolling. These inspection steps in theory detect the existence of flaws in the billet which would produce flaws in the resulting bar product. Once the billet flaws are detected they are removed by scarfing or other procedures. During the rolling of the billet, however, other defects may be introduced. A piece of foreign matter may be stuck to the roll and introduce repetitive elongated scratches or grooves in the steel as rolling occurs. If the rolls become misshaped, they can generate severe irregularities in the steel bar which on subsequent rolling may become folded over to also form elongated grooves or flaws along the bar. If the causes of these defects are not detected as soon as possible, many bars having these defects will be produced.

If the steel bars contain flaws of less than a certain depth, these flaws can be ground out and the bars may be sold for their intended purpose. If, however, the flaws exceed a certain depth, the bars are scrapped and must be reprocessed with loss in productivity and at additional expense. It is apparent that it is desirable to detect the presence of flaws as soon as possible so corrective steps can be taken to eliminate the source of the flaws.

Various prior art patents disclose procedures for detecting the presence of flaws before the product cools. U.S. Pat. No. 4,024,470 to Vild et al. entitled "Eddy Current Detector for Hot Test Pieces Having Cooling Fluid and Purge Features" discloses apparatus where a combination of a heat shield and a fluid coolant protects detectors from the heat of a hot workpiece.

The Vild et al. and a number of other prior art patents relating to eddy current testing are assigned to the Republic Steel Corporation, assignee of the present invention. Republic Steel patents which disclose control circuitry and apparatus to classify and mark the position of defects in steel bars are U.S. Pat. No. 3,108,230 to Judd et al. and U.S. Pat. No. 3,263,809 to Mandula et al. as well as the '470 patent to Vild et al. An improvement to the marking process of these patents is disclosed in recently issued U.S. Pat. No. 4,365,198 to Toth. U.S. Pat. No. 4,355,281 to Toth et al. also concerns an eddy current test arrangement having two detection coils spaced along a workpiece path so that as the workpiece is rotated and translated past the coils flaws are detected. The disclosures of these five patents is incorporated herein by reference.

In a typical eddy current tester, an excitation coil is placed in proximity to a steel object under test. The coil is energized with an electric signal which creates magnetic fields which in turn create eddy currents in the steel. A flaw in the steel disrupts the eddy current flow and this disruption can be sensed by monitoring the induced current in a test coil. A prior art eddy current tester for relatively deep flaws includes both an excitation or energization coil to set up the eddy currents in the workpiece and a separate detector coil which is used in monitoring eddy currents.

Proposals have been made to modify the functioning of these prior eddy current testers. These proposals concern strengthening or enhancing a magnetic field in various locations in relation to a product under test. This enhanced magnetic field produces a stronger response in the test equipment monitoring the eddy currents. The prior proposals include either a shield to selectively transmit a magnetic field to the surface of the product or, in the alternative, a rotatable magnetic field producing element moved in relation to the product. These proposals, while recognizing a desirable effect, i.e. the selective enhancement of the response produced by the excitation coil, were ineffective or inefficient in producing this response.

It is one object of the present invention to improve upon the capabilities of these prior art flaw detectors. Such an improved flaw detector must accurately detect the presence of product degrading flaws at as early a stage of production as possible.

DISCLOSURE OF THE INVENTION

An improved eddy current tester is disclosed for detecting flaws in a workpiece. In accordance with the invention, long flaws extending along an elongated workpiece are detected with enhanced reliability. This testing can be performed while the product is still very hot to avoid production of large amounts of scrap product when the production equipment is itself flawed or malfunctioning.

The eddy current detector includes a conductive coil mounted about a workpiece path of travel to detect the presence of flaws in the workpiece as that workpiece passes through the coil. An excitation circuit is coupled to the coil to excite the coil with an electric signal which produces eddy currents in the workpiece. Analyzing circuitry monitors the eddy currents produced and correlates changes in these eddy currents with flaw locations in the workpiece. Finally, field altering apparatus is mounted in close proximity to the coil to disrupt an induced magnetic field at continuously varying locations about the workpiece. The altering apparatus includes means for orbiting a ferromagnetic object of high magnetic permeability about a path surrounding the workpiece.

The field altering apparatus is positioned outside the workpiece path of travel so hot bar product can be tested without damaging the test apparatus. In one embodiment a ferrite ball is rotated at high speed (about 6000 rpm) inside a circular channel by a compressed air source.

In accordance with a preferred embodiment of the invention, first and second detector coils are mounted at axially displaced locations along the workpiece path of travel. These coils detect the presence of any flaw along the workpiece. To enhance the response of these detector coils, first and second field altering objects are also mounted in close proximity to the coils to disrupt a magnetic field in continuously varying locations about the workpiece near the separate detection coils. The analyzing circuitry responds to the presence of any flaw by giving a clear indication that a flaw is present underneath at least one of the two coils.

A preferred field altering mechanism includes a rotatably mounted, heat resistant sleeve which carries two ferrite objects. The sleeve and accompanying ferrite objects are rotated in tandem by a motor coupled to the sleeve. The angular orientation of the two objects is separated a short distance about the workpiece surface. This angular separation produces clearly detectable positive and negative pulses in the analyzing circuitry when a flaw extends beneath both test coils.

The test fixture for the new and improved tester comprising the present invention is made of ceramic material. This material enables the tester to be located in close proximity to the workpiece even though the workpiece remains at a temperature of over 2000° F. If flaws are detected while a product is still in the process of being produced, the cause of these flaws can be determined and corrected quickly to reduce the number of occasions such flaws are repeated in subsequently produced product.

The method and apparatus of the invention has great utility for use with hot steel bars as they are rolled from billets. The long seams characteristic of flawed production of steel bars can be detected and steps taken to avoid further flawed product. The disclosed detection method can also be used in conjunction with any product where seams or cracks extend along a workpiece and in particular could be used in testing pipe for such flaws.

In this regard, it should be noted that stainless steel or other nonmagnetic objects can be tested. The feature that enhances the detection of flaws or disruptions in the workpiece is electrons that respond to the disruption in the magnetic field rather than the intrinsic magnetic permeability of the workpiece. Indeed, the hot steel bars are tested at temperatures above their Curie Point so they exhibit no intrinsic magnetic permeability.

From the above it should be appreciated that one object of the invention is an improved eddy current tester and a method for detecting flaws along a workpiece surface. Other objects, advantages and features of the present invention will become better understood when a detailed description of a preferred embodiment of the invention is described in conjunction with the accompanying drawings.

BEST MODE FOR CARRYING OUT THE INVENTION

Figure 1:
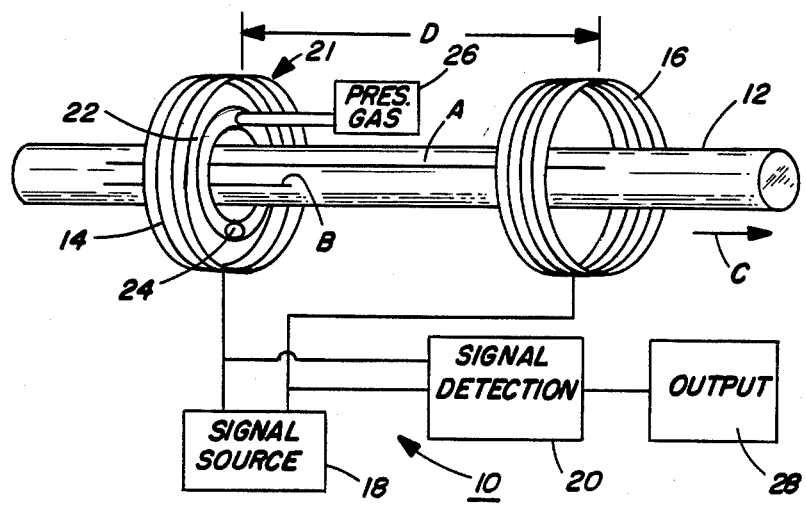
FIG. 1 a schematic perspective view of a workpiece moving along a path circumscribed by two detecting coils.
Figures 2A, 2B, 2C:
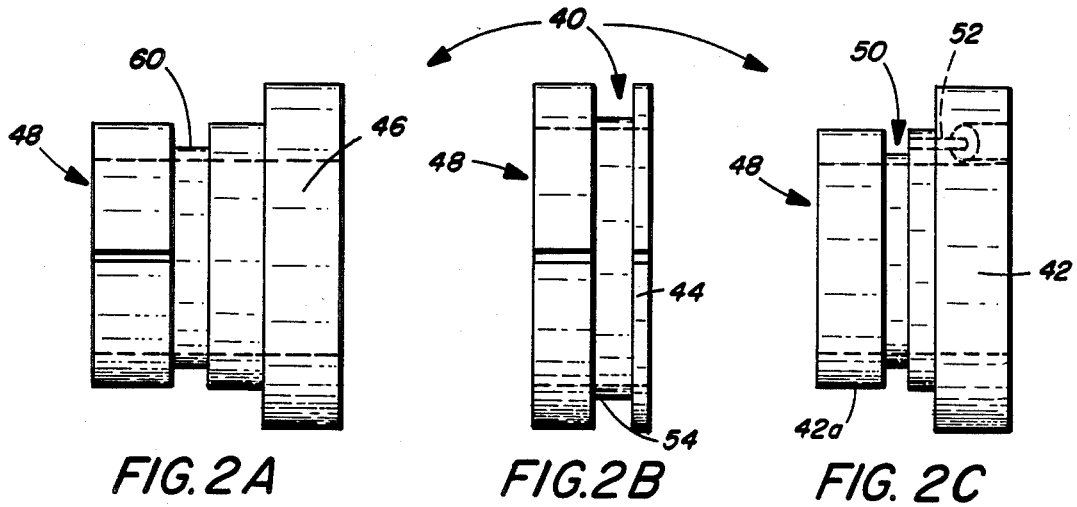
FIGS. 2A–2C are elevation views of structure for supporting said coils in proximity to the workpiece path of travel.
Figure 3:
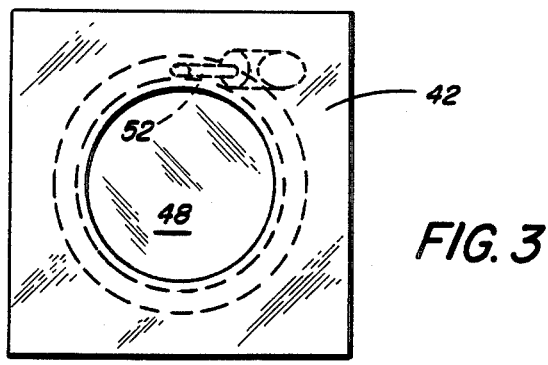
FIG. 3 is an end elevation view of the FIG. 2C mounting structure showing an air inlet for rotating a steel ball circumferentially about the workpiece in the vicinity of one of the detecting coils.
Figure 4:
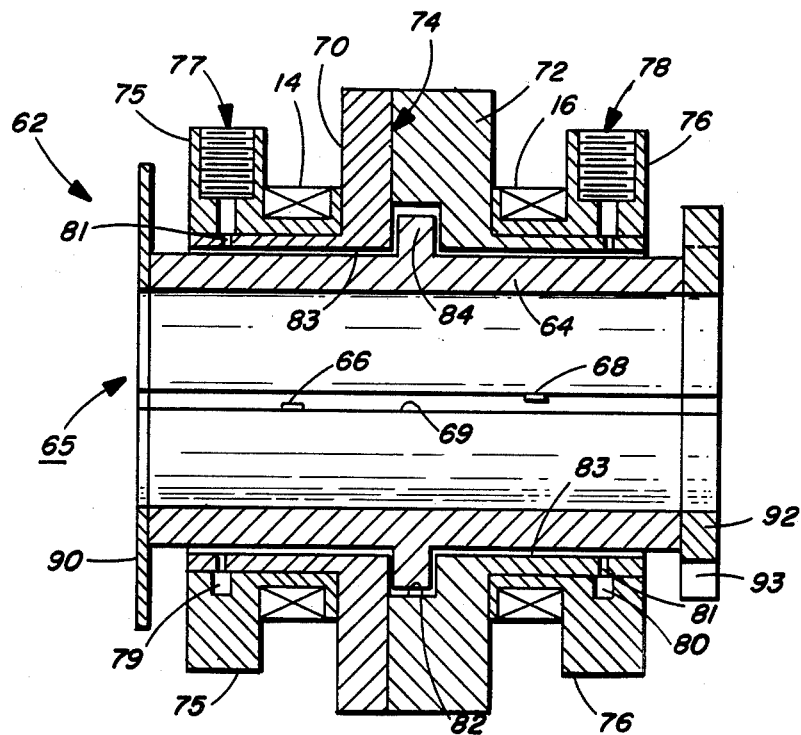
FIGS. 4–7 show alternate and preferred structure for mounting the detecting coils.

Turning now to the drawings, FIG. 1 discloses a flaw detecting apparatus 10 for detecting the presence of flaws A, B, extending along the length of a workpiece 12. This workpiece 12 is moving along a path of travel indicated by the arrow C. Mechanisms for moving an elongated workpiece such as the one shown in the figure are well known in the art and will not be described. One feature of the invention allows the workpiece to be translated without rotation and this feature facilitates construction of the apparatus for moving the workpiece.

The illustrated apparatus 10 includes two multiturn detecting coils 14, 16 spaced a distance D apart along the workpiece path of travel. Each of the detecting coils 14, 16 is shown coupled via a conductor to a signal source 18. The signal source 18 energizes each of the coils with an alternating current signal for producing eddy currents at the surface of the workpiece. The signal source 18 and two detecting coils 14, 16 are coupled in a balanced arrangement. This arrangement is known in the art and is described for example, in U.S. Pat. No. 4,355,281 to Toth et al.

The presence of flaws such as gouges or cracks along the workpiece can be detected by a signal detector 20 also coupled to the two detecting coils 14, 16. The use of balanced coils 14, 16 makes output to the detector 20 less susceptible to changes due to noise, spurious signals and temperature variations. The presence of a flaw within the workpiece disrupts the eddy current set up by the source 18 and produces an output signal characteristic of such flaws.

In accordance with the invention, the flaw detecting apparatus 10 further includes a field modifying device 21 which includes a circular path defining member 22 through which a steel ball 24 is rotated by a source 26 of pressurized gas. As the steel ball 24 rotates, it disrupts the magnetic field generated by the coil 14 to make more detectable the signal created by the presence of a flaw beneath the rotating ball. A preferred frequency of rotation is approximately 6000 cycles per minute and can be adjusted by modifying the pressure from the source 26. An output device 28 such as an oscilloscope provides a visual indication of the output from the signal detector.

A preferred assembly 40 for mounting the two excitation coils 14, 16 as well as for defining a path or chamber for the rotating ball 24 is shown in FIGS. 2A, 2B, 2C and 3. The assembly 40 is made up of three ceramic mounting members 42, 44, 46. Each of the mounting members defines a through passage 48 to accommodate the longitudinal movement of the workpiece 12. The diameter of the through passage 48 can be changed to accommodate different size work members so that a typical monitoring station would have available different size ceramic mounting members 42, 44, 46 for testing different size workpieces.

A first member 42 defines a slot 50 which is bounded by the second ceramic mounting member 44 when this second member 44 is slipped over a reduced diameter portion 42a of the first member 42. During assembly of the detecting apparatus, a steel ball 24 is inserted into the slot and the second mounting member 44 is slipped over the first member 42 so that the slot becomes an enclosed annular ball track with the steel ball in it. The slot 50 communicates to the outside by a passageway 52 defined by the ceramic mounting member 42. This passageway enables the compressed air source 26 to be coupled to the slot 50 for causing rotation of the ball about the workpiece.

The second mounting member 44 defines a second slot 54 for the excitation coil 14. The dimensions of the two mounting members 42, 44 are such that the coil 14 and slot 50 are concentric. Stated another way, the excitation coil 14 is circumferentially around the path of travel defined by the slot 50. The third ceramic mounting member 46 defines an additional slot 60 for the second or balancing coil 16. This coil is therefor axially separated from the first coil with the distance between coils defined by the axial spacing of their respective slots 54, 60.

The above arrangement with the ball path of travel radially within one of the coils 14 maximizes the magnetic field disruption caused by rotation of the ball. Tests have been conducted with the ball path in other positions. It is possible, for example, to design mounting members 42-46 to position the path of movement outside the excitation coil or next to the excitation coil. So long as the ball disrupts the magnetic field produced by energization of the coil, the intended effect occurs.

This FIG. 1 arrangement, with two balanced coils 14, 16 coupled to a common signal source 18 does not distinguish between flaws A and B (unless there is a significant difference in depth betweeen the two) but unlike the prior art, senses flaw A due to the magnetic disruptive affect of the rotating ball 24.

An alternate and preferred mounting apparatus 62 for practicing the invention is shown in FIGS. 4-7. While in the first embodiment the only moving member was the rotating ball which moved about the workpiece path of travel at a speed of approximately 6000 revolutions per minute, in the second embodiment of the invention, a rotating sleeve 64 which defines a workpiece through passage 65 carries two ferrite objects 66, 68 in separate circumferentially offset paths about the workpiece path of travel. The position of the these ferrite objects 66, 68 is chosen such that as they rotate they traverse paths concentric to the exciting coils 14, 16 respectively. These two ferrite objects are mounted on a narrow slot 69 extending the length of the sleeve 64.

In this second embodiment, the magnetic fields set up by the two test coils 14, 16 are disrupted by the rotating ferrite objects 66, 68. This produces a flaw sensing capability the first embodiment cannot attain due to the fact that only a single ball rotates with respect to the moving workpiece. With two rotating ferrite objects the signal detector 20 can distinguish between flaws A and B to further classify the workpiece. A different output is generated if the objects disrupt the fields over a long flaw A than if only one object 66, for example, disrupts the field over the short flaw B.

The sleeve 64 is axially located by two stationary collars 70, 72 which clamp together along a surface 74 and then are appropriately mounted along the workpiece path of travel. The collars 70, 72 extend axially along the workpiece beneath two abutting generally U shaped coil mounting minor image members 75, 76. The coil mounting members 75, 76 include air inputs 77, 78 couplable to a pressurized source of air (not shown). The coil mounting members 75, 76 further define internal circular slots 79, 80 extending circumferentially around the workpiece path of travel and coupled to these air inputs 77, 78. At equally spaced intervals a plurality of small openings 81 extending through the collars provide fluid communication between the circumferential slots 79, 80 and an annular space defined by the sleeve 64 and inside surface 83 of the collars. Compressed air passing through these openings 81 provides an air bearing for the rotating sleeve 64.

The axial position of the sleeve 64 is fixed once the two collars 70, 72 are clamped together. This is accomplished via a slot 82 defined by the collar 72 (FIG. 4) in which a flange 84 on the sleeve 64 is positioned.

Connected to the sleeve, 64 by suitable connectors is a synchronizing dish 90 which defines a slot that is sensed by a sensor on each rotation of the sleeve 64 on an input side of the workpiece path of travel. On the output side of the workpiece path of travel a drive member 92 having blades or vanes 93 is driven by a compressed air source (not shown) to rotate the sleeve 64 at a desired speed of rotation.

One distinction between the mechanism 62 and the earlier embodiment 40 is that rather than relying upon forced air rotation of a ferrite material, the alternate mechanism 62 utilizes a motor drive to rotate ferrite objects 66, 68 in circumferential paths about the workpiece path of travel. As was the case for the earlier embodiment, these ferrite objects are surrounded by the two test coils 14, 16.

This alternate mechanism 62 is particularly adapted for detecting elongated flaws extending significant distances along the workpiece 12. The flaw A extends the distance D between the two coils 14, 16. The first embodiment of the invention wherein a steel ball is rotated inside the first excitation coil 14 is incapable of distinguishing between the elongated flaw A and the significantly shorter flaw B.

Using the alternate mechanism 62, however, simultaneous (or as will be seen nearly simultaneous) detection of the presence of the elongated flaw A by the two separated test coils 14, 16 indicates the flaw extends beneath both coils and therefore has a length equal to or greater than D, the separation between coils.

Figure 8:
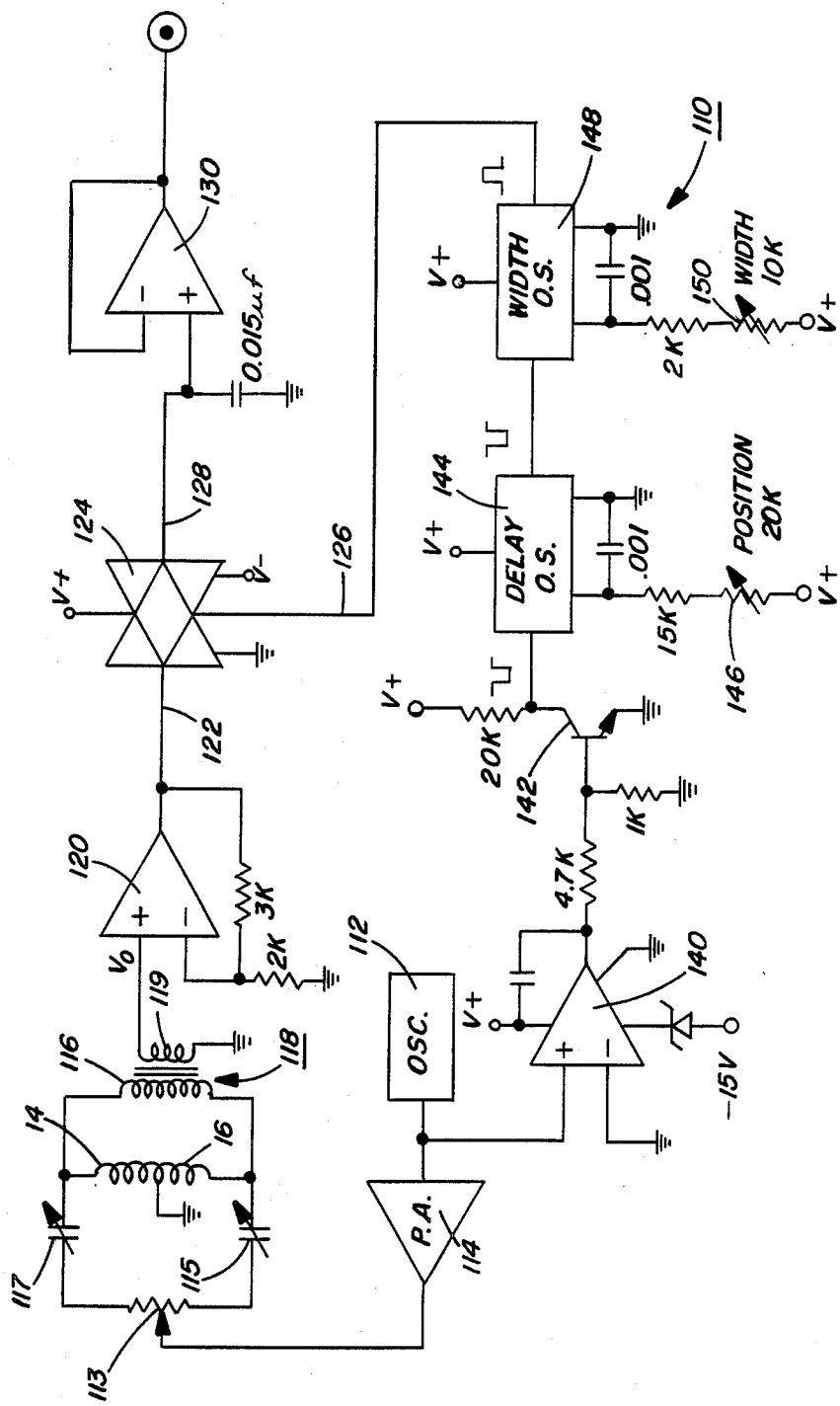
FIG. 8 is an electrical schematic showing circuitry for analyzing signal outputs from the two detecting coils.

Circuitry 110 for energizing and evaluating output signals from the two test coils 14, 16 is schematically illustrated in FIG. 8. In that figure an oscillator 112 is seen driving a power amplifier 114 which in turn is coupled to the two coils 14, 16. Interposed between the power amplifier 114 and coils 14, 16 are variable resistor 113 and two phase shifting variable capacitors 115, 117. These components allow the relative magnitude and phase of the alternating signals across the coils to be adjusted to enhance sensitivity of the flaw sensing. The frequency output from the oscillator 112 is adjustable and in a preferred embodiment is adjusted to produce a sinusoidal output having a frequency of approximately 40 kilohertz. This energization of the two coils 14, 16 sets up magnetic fields which induce eddy currents at the surface of the workpiece.

When these eddy currents are disrupted by the presence of a flaw, the self induced current through the coils 14, 16 is also disrupted. The interaction of the fields from the coils, the ferrite objects and the workpiece results in a spike or a pulse output from the coils which is sensed by a primary 116 of a transformer 118. The output from a secondary 119 of the transformer 118 is coupled to an amplifier 120 having an output 122 coupled to an analog switch 124. The analog switch 124 has a gate input 126 which selectively transmits signals from the input 122 through the switch to an output 128 which in turn is buffered by an amplifier 130. An output from this buffer 130 is transmitted to analyzing circuitry which counts the seams as well as analyzing their severity.

One system for analyzing the severity of the defects is disclosed in U.S. Pat. No. 190 4,365,198 to Toth entitled "Method and Apparatus For Detecting, Classifying, and Marking Defects in a Workpiece with Improved Timing Control" which issued Dec. 21, 1982 and is incorporated herein by reference.

A gate signal for the gate input 126 also originates at the oscillator 112. The gate signal is a square pulse which periodically couples the analog gate input 122 to its output 128. An output from the oscillator 112 is coupled to a buffer amplifier 140 which generates an alternating current signal to a switching transistor 142 for converting the analog output from the oscillator 112 into a series of pulses. A first one shot 144 produces a delay of from 7 to 16 microseconds depending on the setting of a variable 20k resistor 146. A second one shot 148 varies the width of its output pulse from one to five microseconds depending on the setting of a 10k variable resistor 150.

A 40 kilohertz oscillator output produces a time or period between peak-to-peak signals of 25 microseconds. The ability to shift and shape the gating signal within this 25 microsecond period allows the user to maximize the output 128 and therefore the sensitivity of the flaw detection.

Figure 9:
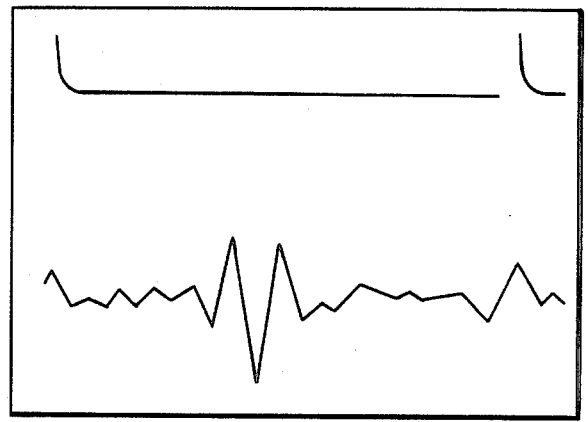
FIGS. 9 and 10 are voltage versus time plots of outputs from the FIG. 8 circuitry.
Figure 10:
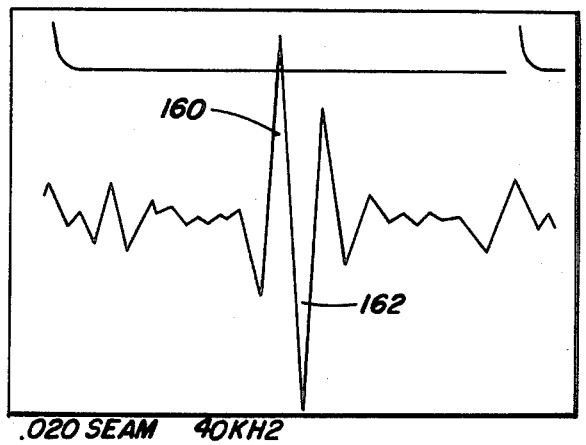

When the output from the amplifier 130 is filtered and coupled to an oscilloscope, and the sweep rate of the oscilloscope scanning beam is synchronized by the signals generated by sensing rotation of the disk 90, the FIG. 9 and 10 oscilloscope images are generated by longitudinal flaws extending beneath both coils 14, 16. It is seen that the 0.010 inch deep seam is clearly noticeable and the 0.020 inch deep seam produces output spikes clearly distinguishable from all other signal variations on the screen. The oscilloscope sweep rate and vertical gain are the same for both figures.

Figure 5:
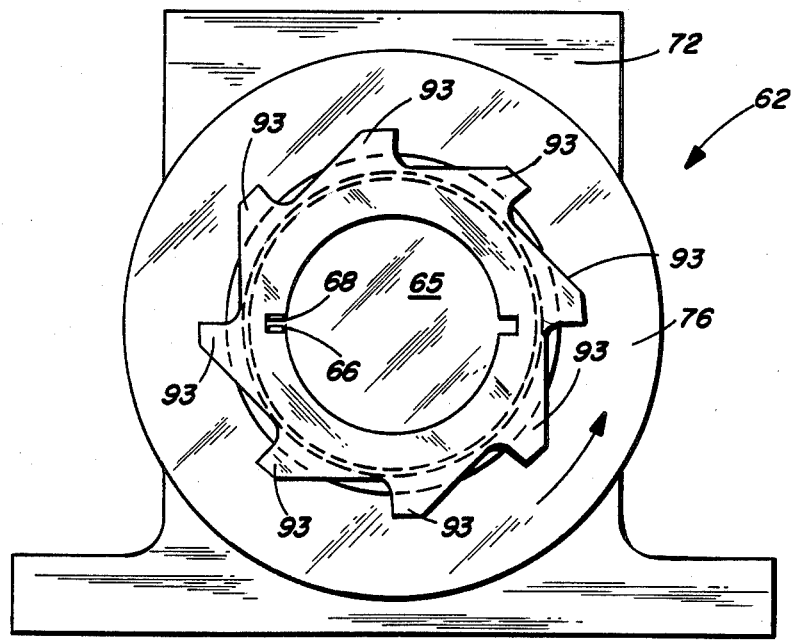
Figure 6:
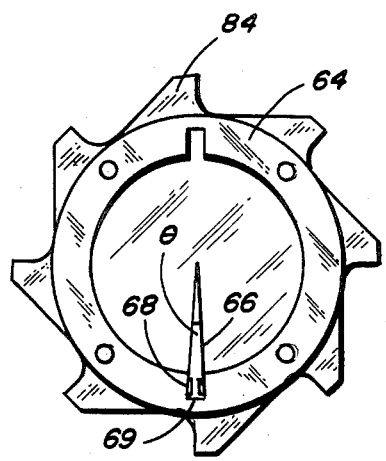
Figure 7:
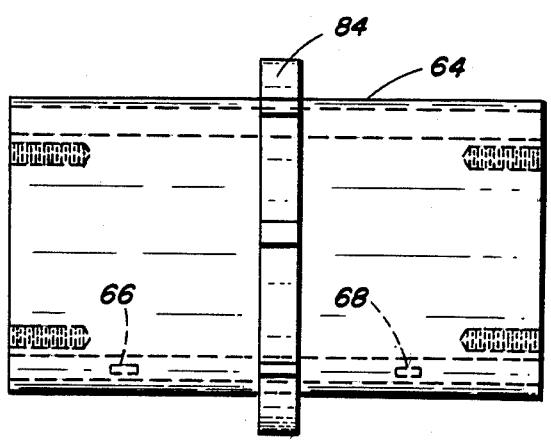

The positive and negative closely adjacent spikes are attributable to first one and then the other of the two ferrite objects 66, 68. Assume counterclockwise rotation of the sleeve 64 as seen in FIG. 5. As the ferrite object 66 passes over a 0.020 inch seam A (for example) a sharp positive going spike 160 appears on the scope. A short time later the second ferrite object 68 passes the same seam A and the sharp negative spike 162 appears as an output. Analyzing circuitry for measuring the slope of the filtered output records a large negative slope and indicates the presence of a flaw.

The purpose in the small angular offset $\theta$ (Figure 6) between the two ferrite objects 66, 68 is now apparent. If both objects 66, 68 were to pass over the flaw A at the same time the outputs 160, 162 would cancel and no signal would be seen.

Details of filtering and bar classifying circuitry suitable for use with the disclosed apparatus are available in a co-pending U.S. patent application entitled "Eddy Current Flaw Detector Having Rotatable Field Defining Sleeve" to Harris et al. Ser. No. 625,029 assigned to the Republic Steel Corporation and incorporated herein by reference.

The analyzing circuitry 110 will also work for the rotating steel ball embodiment of the invention. In this embodiment all output pulse will be of the same polarity (either positive or negative depending on which coil the ball rotates in proximity to) so an appropriate modification in the analyzing circuitry coupled to the output 128 is needed. For short flaws B, the circuitry 110 will also provide a single polarity output rather than the closely adjacent positive and negative spikes. A means for distinguishing between flaws A and B is thus provided.

The invention has been described with a degree of particularity. It is the intent, however, that the invention include all alterations or modifications of the specific disclosed embodiment falling within the spirit or scope of the appended claims.

We claim:

1. Eddy current test apparatus for detecting flaws in a workpiece comprising:
   two differentially wound conductive coils coaxial with each other and spaced along a workpiece path of travel for detecting the presence of flaws in said workpiece as said workpiece passes through said coils;
   excitation circuitry coupled to said coils for exciting said coils with an electrical signal to induce eddy currents at spaced locations beneath said coils;
   detection circuitry for monitoring eddy currents in the workpiece at the spaced locations beneath said coils and for correlating changes in said eddy currents with flaw locations in the workpiece; and
   field altering means mounted in close proximity to one of said detection coils to distort a magnetic field at changing locations along a workpiece surface of interest, said field altering means including an enclosed annular track that encircles the workpiece path near the workpiece surface of interest, a ball having a high magnetic permeability positioned within the enclosed annular track, and a source of pressurized fluid coupled to an interior of the enclosed annular track to drive said ball about said workpiece path.

2. An eddy current tester for detecting flaws in a workpiece comprising:
   first and second differentially wound detector coils mounted at axially displaced locations along a workpiece path of travel and encircling said path of travel to detect the presence of flaws at least as long as the axial displacement between coils as a workpiece moves along said path;
   excitation means coupled to said two coils to excite said coils with an electrical signal thereby inducing eddy currents in such workpiece at said spaced locations;
   analyzing circuitry also coupled to said coils to monitor eddy currents in such workpiece and to correlate changes in said eddy currents with flaws extending along such workpiece between said coils; and field concentrating means mounted in close proximity to said detection coils to concentrate a magnetic field at continuously varying locations about said workpiece path, said field concentrating means including
- (i) a generally cylindric, metallic sleeve mounted for rotation about the workpiece path of travel radially inward of the detector coils, and
- (ii) two objects of high magnetic permeability coupled to the metallic sleeve for rotation along separate object paths around said workpiece path beneath said two coils in circumferentially offset relation to cause said objects to pass over an elongated flaw extending beneath the first and second differentially wound detector coils at different times.

3. The eddy current tester of claim 2 wherein a first orbital path for a first orbiting object is concentric with at least a portion of said first detector coil and a second orbital path for a second orbiting object is concentric with at least a portion of a second detector coil.

4. The eddy current tester of claim 2 wherein the first and second detector coils are coupled together at a common ground connection and wherein noncommon ends of said coils are connected to said excitation means, said excitation means including circuitry for accepting a single alternating current signal and generating two wave shifted alternating current signals of the same polarity for transmittal to said noncommon ends.

5. A method for detecting flaws in a workpiece comprising the steps of:

moving a workpiece along a path through two differentially wound co-axially aligned conductive coils spaced from each other along the workpiece travel path;

exciting said coils with an electric signal to create a magnetic field, said field generating eddy currents in said workpiece;

distorting the magnetic field beneath one of the spaced coils by orbiting a high magnetic permeability ball in a circular track next to the workpiece concentric with said one coil by applying a fluid pressure against the ball; and correlating flaw locations in said workpiece with changes in eddy current as said object is moved about said workpiece by monitoring electrical signals in said two coils.

* * * * *